United States Patent [19]
Neumann et al.

[11] Patent Number: 5,248,498
[45] Date of Patent: Sep. 28, 1993

[54] FULLERENE COMPOSITIONS FOR MAGNETIC RESONANCE SPECTROSCOPY AND IMAGING

[75] Inventors: William L. Neumann, Grover; William P. Cacheris, Florissant, both of Mo.

[73] Assignee: Mallinckrodt Medical, Inc., St. Louis, Mo.

[21] Appl. No.: 746,836

[22] Filed: Aug. 19, 1991

[51] Int. Cl.$^5$ ............... G01N 24/08; C07C 19/08; C01F 17/00; C01B 31/02
[52] U.S. Cl. .................... 424/9; 534/15; 423/263; 423/445; 436/173; 128/653.4; 570/130
[58] Field of Search ........... 424/9, 1.1; 423/263, 423/445; 436/173; 128/653.4, 654; 570/130; 534/15

[56] References Cited

U.S. PATENT DOCUMENTS

| | | | |
|---|---|---|---|
| 4,647,447 | 3/1987 | Gries et al. | 424/9 |
| 5,114,477 | 5/1992 | Mort et al. | 106/20 |
| 5,132,105 | 7/1992 | Remo | 423/446 |

OTHER PUBLICATIONS

Kroto, H. W. et al. Nature 318: 162-3 (1985).

F. Diederich, "From Soot to Superconductors", *Angew. Chem. Int. Ed. Engl.*, vol. 30, No. 6, pp. 678-680 (1991).
H. Selig, et al., "Fluorinated Fullerenes", *J. Am. Chem. Soc.*, vol. 113, pp. 5475-5476 (1991).
Alan L. Mackay, "Carbon Crystals Wrapped Up", *Nature*, vol. 347, pp. 336-337 (1990).
Harold Kroto, "Space, Stars, $C_{60}$ and Soot", *Science*, vol. 242, pp. 1139-1145 (1988).
W. Krätschmer et al., "Solid $C_{60}$: a new form of carbon", *Nature*, vol. 347, pp. 336-337 (1990).
Rudy M. Baum, "Simple Synthesis of $C_{60}$ Molecule Triggers Intense Research Effort", *Chemical and Engineering News*, pp. 22-25 (Oct. 29, 1990).

*Primary Examiner*—Allen J. Robinson
*Assistant Examiner*—Gary E. Hollinden
*Attorney, Agent, or Firm*—Madson & Metcalf

[57] ABSTRACT

Methods and compositions are disclosed for enhancing magnetic resonance imaging and spectroscopy which utilize derivatives of the even-numbered carbon clusters, known as "fullerenes." Perfluorinated carbon clusters of the formula $C_nF_m$, wherein n is in the range from 30-100 and $m \leq n$, may be used for fluorine-19 imaging. Incorporating paramagnetic metal species into the carbon cluster cage improves fluorine and proton imaging.

17 Claims, 2 Drawing Sheets

FULLERENE COMPOSITIONS FOR MAGNETIC RESONANCE SPECTROSCOPY AND IMAGING

BACKGROUND OF THE INVENTION

This invention relates to compositions for improving magnetic resonance imaging ("MRI"), magnetic resonance spectroscopy ("MRS"), and magnetic resonance spectroscopy imaging ("MRSI"). More particularly, the present invention relates to low concentration fluorine-19 imaging agents.

The technique of MRI encompasses the detection of certain atomic nuclei (those possessing magnetic dipole moments) utilizing magnetic fields and radio-frequency radiation. It is similar in some respects to X-ray computed tomography ("CT") in providing a cross-sectional display of the body organ anatomy with excellent resolution of soft tissue detail. The technique of MRI is advantageously non-invasive as it avoids the use of ionizing radiation.

The hydrogen atom, having a nucleus consisting of a single unpaired proton, has the strongest magnetic dipole moment of any nucleus. Since hydrogen occurs in both water and lipids, it is abundant in the human body. Therefore, MRI is most commonly used to produce images based upon the distribution density of protons and/or the relaxation times of protons in organs and tissues. Other nuclei having a net magnetic dipole moment also exhibit a nuclear magnetic resonance phenomenon which may be used in MRI, MRS, and MRSI applications. Such nuclei include carbon-13 (six protons and seven neutrons), fluorine-19 (9 protons and 10 neutrons), sodium-23 (11 protons and 12 neutrons), and phosphorus-31 (15 protons and 16 neutrons).

While the phenomenon of NMR was discovered in 1945, it is only relatively recently that it has found application as a means of mapping the internal structure of the body as a result of the original suggestion of Lauterbur (*Nature*, 242, 190-191 (1973)). The fundamental lack of any known hazard associated with the level of the magnetic and radio-frequency fields that are employed renders it possible to make repeated scans on vulnerable individuals. Additionally, any scan plane can readily be selected, including transverse, coronal, and sagittal sections.

In an MRI experiment, the nuclei under study in a sample (e.g. protons, $^{19}F$, etc.) are irradiated with the appropriate radio-frequency (RF) energy in a controlled gradient magnetic field. These nuclei, as they relax, subsequently emit RF energy at a sharp resonance frequency. The resonance frequency of the nuclei depends on the applied magnetic field.

According to known principles, nuclei with appropriate spin when placed in an applied magnetic field (B, expressed generally in units of gauss or Tesla ($10^4$ gauss)) align in the direction of the field. In the case of protons, these nuclei precess at a frequency, F, of 42.6 MHz at a field strength of 1 Tesla. At this frequency, an RF pulse of radiation will excite the nuclei and can be considered to tip the net magnetization out of the field direction, the extend of this rotation being determined by the pulse, duration and energy. After the RF pulse, the nuclei "relax" or return to equilibrium with the magnetic field, emitting radiation at the resonant frequency. The decay of the emitted radiation is characterized by two relaxation times, $T_1$ and $T_2$. $T_1$ is the spin-lattice relaxation time or longitudinal relaxation time, that is, the time taken by the nuclei to return to equilibrium along the direction of the externally applied magnetic field. $T_2$ is the spin-spin relaxation time associated with the dephasing of the initially coherent precession of individual proton spins. These relaxation times have been established for various fluids, organs, and tissues in different species of mammals.

In MRI, scanning planes and sliced thicknesses can be selected. This selection permits high quality transverse, coronal and sagittal images to be obtained directly. The absence of any moving parts in MRI equipment promotes a high reliability. It is believed that MRI has a greater potential than CT for the selective examination of tissue characteristics. The reason for this being that in CT, X-ray attenuation and coefficients alone determine image contrast, whereas at least four separate variables ($T_1$, $T_2$, proton density, and flow) may contribute to the MRI signal. For example, it has been shown (Damadian, *Science*, 171, 1151 (1971)) that the values of the $T_1$ and $T_2$ relaxation in tissues are generally longer by about a factor of two (2) in excised specimens of neoplastic tissue compared with the host tissue.

By reason of its sensitivity to subtle physiochemical differences between organs and/or tissues, it is believed that MRI may be capable of differentiating different tissue types and in detecting diseases which induce physicochemical changes that may not be detected by X-ray or CT which are only sensitive to differences in the electron density of tissue.

As noted above, two of the principal imaging parameters are the relaxation times, $T_1$ and $T_2$. For protons and other suitable nuclei, these relaxation times are influenced by the environment of the nuclei (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby nuclei having a magnetic dipole moment. The extent of the paramagnetic effect of the given chemical compound is a function of the environment within which it finds itself.

In general, paramagnetic ions of elements with an atomic number of 21 to 29, 42 to 44 and 58 to 70 have been found effective as MRI contrasting agents. Suitable such ions include chromium (III), manganese (II), manganese (III), iron (III), iron (II), cobalt (II), nickel (II), copper (II), praseodymium (III), neodymium (III), samarium (III) and ytterbium (III). Because of their very strong magnetic moments, gadolinium (III), terbium (III), dysprosium (III), holmium (III) and erbium (III) are preferred. Gadolinium (III) ions have been particularly preferred as MRI contrasting agents.

In some cases, the concentration of nuclei to be measured is not sufficiently high to produce a detectable MR signal. For instance, since $^{19}F$ is present in the body in very low concentration, a fluorine source must be administered to a subject to obtain a measurable MR signal. Signal sensitivity is improved by administering higher concentrations of fluorine or by coupling the fluorine to a suitable "probe" which will concentrate in the body tissues of interest. High fluorine concentration must be balanced with increased tissue toxicity. It is also currently believed that any fluorine agent should contain magnetically equivalent fluorine atoms in order to obtain a clear, strong signal.

From the foregoing, it would be a significant advancement in the art to provide fluorine MRI agents for enhancing images of body organs and tissues which may be administered in relatively low concentrations, yet provide a clear, strong signal. It would also be improvement in the art to provide novel MRI agents which include paramagnetic metal species that enhance magnetic resonance results.

Such MRI agent are disclosed and claimed herein.

SUMMARY OF THE INVENTION

The present invention provides methods and compositions for improved magnetic resonance imaging and spectroscopy, including fluorine-19 MRI agents. The MRI agents are derived from the class of even-numbered carbon clusters referred to in the art as fullerenes. Fullerenes range in size from $C_{30}$ to $C_{100}$, with even larger clusters theoretically predicted. These stable closed carbon shells are extracted from the soot of vaporized graphite. The highly stable $C_{60}$ compound is marked by an icosahedral-cage structure, typified by a soccer ball. Some of the more common fullerene structures are illustrated in FIG. 1.

Since $C_{60}$ exhibits extended aromaticity and has been found to be a sensitizer, chemical modification of the $C_{60}$ structure is necessary to prepare compositions suitable for in vivo applications. Hydrogenated, fluorinated, heterocyclic, and other functionalized derivatives of the $C_{60}$ structure have been prepared. Importantly, it is also possible to incorporate metal species into the carbon cage. By vaporizing graphite impregnated with paramagnetic metal species, it is possible to produce fullerene cages containing a paramagnetic metal species. The fullerene cages may then be fluorinated or hydrogenated to form a stable, nontoxic composition. The presence of a paramagnetic metal species may reduce $^{19}F$ and proton relaxivity, thereby enhancing MRI, MRS, or MRSI.

Because the perfluorinated structure $C_{60}F_{60}$ has a high molar content of identical fluorine atoms, $C_{60}F_{60}$ is advantageously used as a low concentration $^{19}F$ MRI agent. Being an inert polyfluorinated hydrocarbon, it is also believed that perfluorinated fullerenes may be used as blood substitutes or be used to obtain magnetic resonance images of blood flow and perfusion.

Also disclosed are diagnostic compositions and methods of performing MR diagnostic procedures which involve administering to a warm-blooded animal a diagnostically effective amount of the above-described fullerene derivatives and then exposing the warm-blooded animal to a MR procedure.

DETAILED DESCRIPTION OF THE INVENTION

Figure 1:
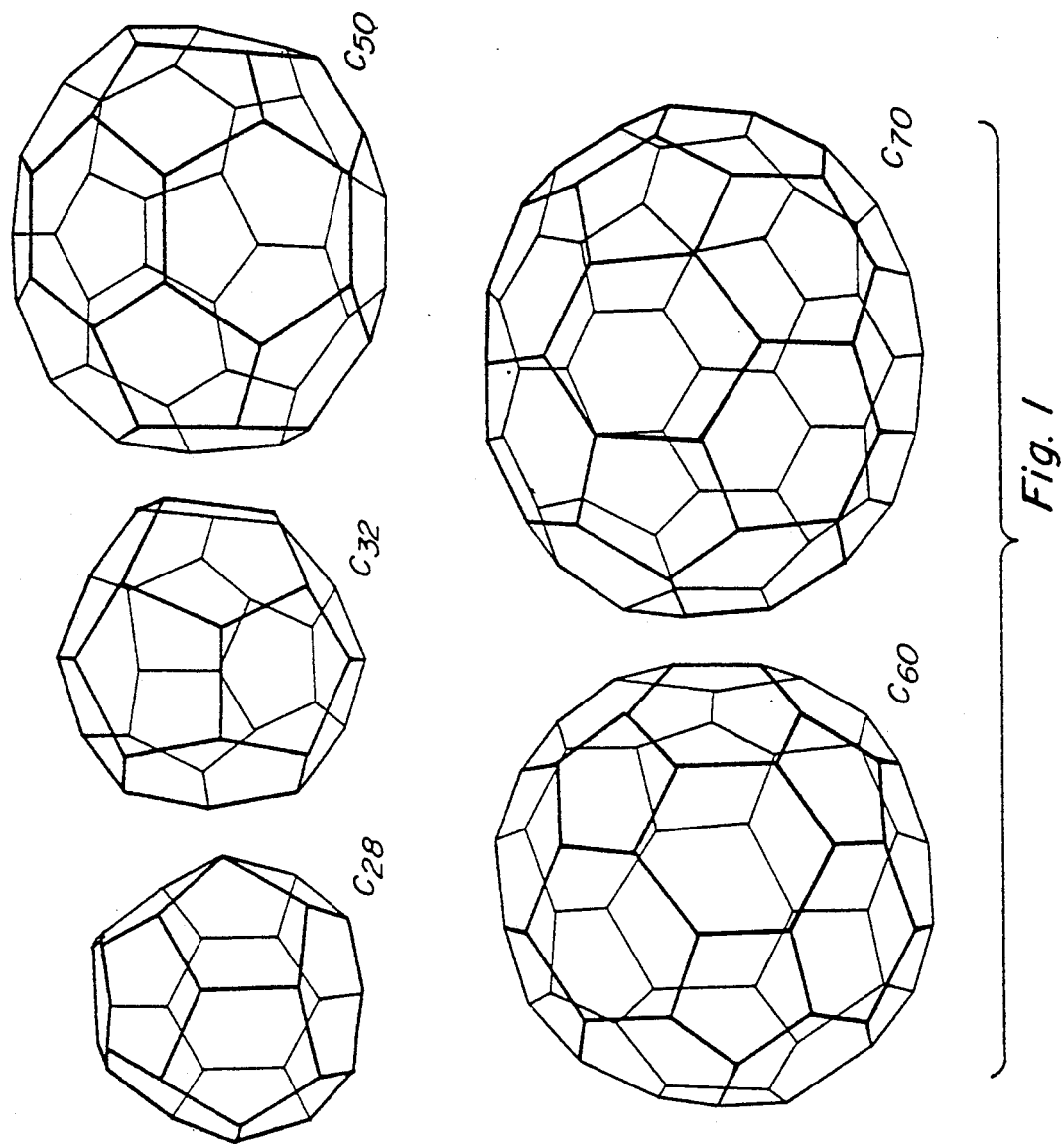
FIG. 1 illustrates the structures of the common fullerenes $C_{26}$, $C_{32}$, $C_{50}$, $C_{60}$, and $C_{70}$.

The present invention provides novel MRI agents, including fluorine MRI agents. The MRI agents are derived from even-numbered carbon clusters in the range $C_{30}$–$C_{100}$. These stable closed carbon shells have recently been isolated from vaporized graphite. The highly stable $C_{60}$ compound is marked by an icosahedral-cage structure, a polygon with 60 equivalent vertices, 32 faces, 12 of which are pentagonal and 20 hexagonal. The icosahedral structure is typified by a soccer ball. The $C_{60}$ structure has been given the name "buckminsterfullerene" due to its similarity to the geodesic domes of Buckminster Fuller. The class of closed cage, carbon clusters is commonly referred to as "fullerenes." The structures of a variety of fullerenes ($C_{28}$, $C_{32}$, $C_{50}$, $C_{60}$, and $C_{70}$) are illustrated in FIG. 1.

$C_{60}$ is the prototypical fullerene. A number of methods for the formation and purification of $C_{60}$ have been developed and are known in the art. Generally, pure graphitic carbon is vaporized in an inert atmosphere, and $C_{60}$ is extracted from the deposited soot with benzene, toluene, carbon disulfide, or carbon tetrachloride. The extract consists primarily of $C_{60}$ and $C_{70}$. Other stable low molecular weight fullerenes have also been identified, such as $C_{24}$, $C_{28}$, $C_{32}$, and $C_{50}$. The existence of high molecular weight fullerenes, such as $C_{240}$ and $C_{540}$, is theoretically predicted.

Since $C_{60}$ exhibits extended aromaticity and has been found to be a sensitizer, chemical modification of the $C_{60}$ structure is necessary to prepare compositions suitable for in vivo applications. Hydrogenation of fullerenes is achieved using known techniques, such as catalytic hydrogenation or dissolving metal reduction. The partially hydrogenated compounds, $C_{60}H_{36}$ and $C_{60}H_{18}$, are readily formed. Complete hydrogenation to $C_{60}H_{60}$ by catalytic hydrogenation may be accomplished using higher pressures of $H_2$ and variation of catalyst.

Figure 2:
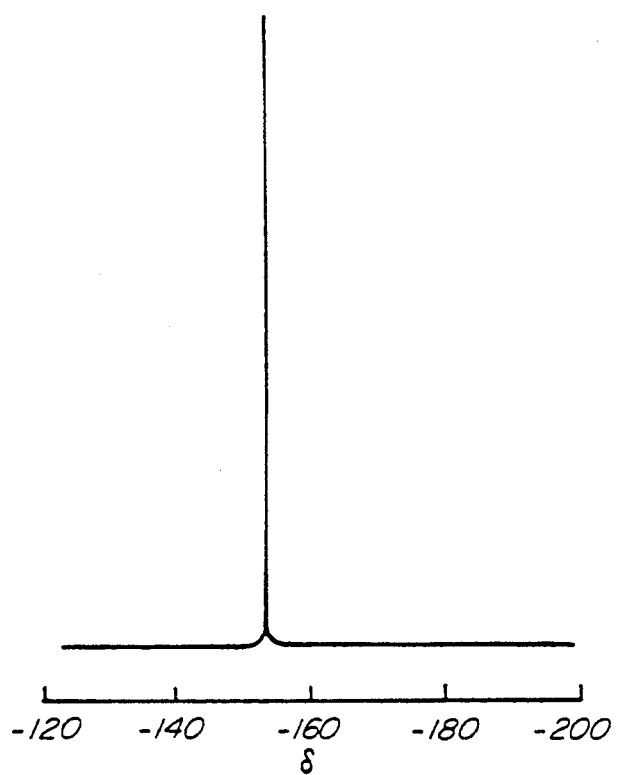
FIG. 2 is a representation of the NMR spectrum for $C_{60}F_{60}$.

The perfluorinated derivative $C_{60}F_{60}$ may be prepared by direct fluorination of $C_{60}$ with fluorine gas at 70° C. Holloway, J., et al., "Fluorination of Buckminsterfullerene," *J. Chem. Soc., Chem. Commun.*, pp. 966–969, 1991; Selig, H., et al., "Fluorinated Fullerenes," *J. Am. Chem. Soc.*, Vol. 113, pp. 5475–5476. Due to the ioosahedral symmetry all of the carbon and fluorine atoms in $C_{60}F_{60}$ are chemically and magnetically equivalent. The $^{19}F$ NMR spectrum confirms this with only one resonance at $\delta -153.9$. FIG. 2 is an illustration of the $^{19}F$ NMR spectrum. Since $C_{60}F_{60}$ has a high molar content of identical fluorine atoms, $C_{60}F_{60}$ may be advantageously used as a low concentration $^{19}F$ MRI agent.

Because of the high molar fluorine content, perfluorinated fullerenes should be able to retain and release large quantities of oxygen, making them ideal blood substitutes. Perfluorinated fullerenes may also be used to obtain magnetic resonance images of blood flow and perfusion as a blood pool imaging agent.

By vaporizing graphite impregnated with a suitable paramagnetic metal species, it is possible to produce fullerene cages containing a paramagnetic metal species. The term paramagnetic metal species as used herein includes within its scope both paramagnetic atoms and ions. The fullerene cages may then be fluorinated or hydrogenated as described above. The presence of a paramagnetic metal species may reduce $^{19}F$ and proton relaxivity, thereby enhancing MRI, MRS, or MRSI.

It is also believed that incorporating a paramagnetic metal species into the center of the fullerene cage will increase the dipole moment of the entire cage. This may render the cluster water soluble and reduce in vivo toxicity.

The fullerene derivatives of this invention are preferably formulated into diagnostic compositions for enteral or parenteral administration. The fullerene derivatives may be fluorinated for $^{19}F$ imaging and/or contain a diagnostically effective amount of a paramagnetic metal species along with conventional pharmaceutical carriers and excipients appropriate for the type of administration contemplated. For example, parenteral formulations for $^{19}F$ imaging advantageously contain a sterile aqueous solution or suspension of a perfluorinated carbon cluster $C_nF_m$ according to this invention. Various techniques for preparing suitable pharmaceutical solutions and suspensions are known in the art. When a paramagnetic metal species is also incorporated into the carbon cluster, the parenteral formulation would typically contain a perfluorinated carbon cluster, $C_mF_mM^{z+}$, where n is in the range from about 30 to about 100 and $m \leq n$, M is a paramagnetic metal ion, and z is the valence charge in the range from about 1–5. Such solutions also may contain pharmaceutically acceptable buffers and, optionally, electrolytes such as sodium chloride.

Advantageously, the compositions may further contain physiologically acceptable non-toxic cations in the form of a gluconate, chloride or other suitable organic or inorganic salts, including suitable soluble complexes with a chelate/ligand to enhance safety. A cation-ligand complex is preferably provided in amounts ranging from about 0.001 mole percent to about 15 mole percent excess, of the ligand-metal complex. Examples of such physiologically acceptable non-toxic cations include sodium ions, calcium ions, magnesium ions, copper ions, zinc ions and the like including mixtures thereto. Calcium ions are preferred.

Parenteral compositions may be injected directly or mixed with a large volume parenteral composition for systemic administration.

Formulations for enteral administration may vary widely, as is well-known in the art. In general, such formulations include a diagnostically effective amount of the carbon cluster derivatives, which encapsulate a paramagnetic metal species and/or are perfluorinated, in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the degree of fluorination, the particular paramagnetic metal species encapsulated, the organs or tissues which are the subject of the imaging procedure, the NMR imaging equipment being used, etc.

The diagnostic compositions of this invention are used in a conventional manner in magnetic resonance procedures. Compositions may be administered in a sufficient amount to provide adequate visualization, to a warm-blooded animal either systemically or locally to an organ or tissues to be imaged, and the animal then subjected to the MRI procedure. The compositions enhance the magnetic resonance images obtained by these procedures. In addition to their utility and magnetic resonance imaging procedures, the carbon clusters described herein may also be adapted for delivery of radiopharmaceuticals or heavy metals for X-ray contrast into the body by incorporating a radioisotope or heavy metal into the fullerene cage.

The following examples are offered to further illustrate the present invention. These examples are intended to be purely exemplary and should not be viewed as a limitation on any claimed embodiment.

EXAMPLE 1

Preparation of $C_{60}$ "Buckminsterfullerene"

Substantially pure graphite is vaporized by resistive heating under a helium atmosphere. The deposited soot is extracted with boiling benzene or toluene to give a brown-red solution. Evaporation under nitrogen yields a black crystalline material in 14% yield that consists primarily of $C_{60}$ and $C_{70}$. Subsequent analysis shows that the material is about 85% $C_{60}$ and about 15% $C_{70}$. Substantially complete separation of the $C_{60}/C_{70}$ mixture is achieved by column chromatography on neutral alumina with hexanes. The $C_{60}$ fraction is about 99.85% pure and the $C_{70}$ is about 99% pure.

EXAMPLE 2

Fluorination of $C_{60}$

A quantity of solid $C_{60}$, prepared according to the procedure of Example 1, is fluorinated by exposure to fluorine gas at high pressure and 70° C. Substantially complete fluorination is obtained after about twelve days exposure to the fluorine gas. The resulting fluorinated compound, $C_{60}F_{60}$, is soluble in THF and acetone, but insoluble in chloroform. The $^{19}F$ NMR spectra gives a sharp singlet at $\delta -153.9$, suggesting that the fluorines are equivalent. This is illustrated in FIG. 2.

EXAMPLE 3

Hydrogenation of $C_{60}$

A quantity of solid $C_{60}$, prepared according to the procedure of Example 1, is hydrogenated using the Birch reduction process. The Birch reduction process is a conventional dissolving metal (Li°, Na°, K° in liquid ammonia) technique. The reaction converts the dark-colored $C_{60}$ to an off-white substance. Subsequent analysis suggests that two components are present, $C_{60}H_{36}$ and $C_{60}H_{18}$. The Birch reduction is readily reversed by treating the reduction product with a highly selective oxidizing agent, such as 2,3-dichloro-5,6-dicyanobenzoquinone ("DDQ"). Catalytic hydrogenation, using conventional catalysts and techniques, may also be used to hydrogenate $C_{60}$.

EXAMPLE 4

Preparation of a Carbon Cluster Incorporating A Paramagnetic Metal Species

Paramagnetic metal species are incorporated into fullerene cages by laser vaporization of graphite impregnated with the metal. To prepare a carbon cluster containing gadolinium, graphite is first impregnated with gadolinium and subsequently vaporized by laser energy. The deposited soot is collected and gadolinium carbon clusters are extracted. The extracted clusters may then be fluorinated or hydrogenated according to the procedures of Examples 2 or 3, respectively, to prepare MRI Agents within the scope of the present invention.

From the foregoing, it will be appreciated that the present invention provides fluorine MRI agents for enhancing images of body organs and tissues which may be administered in relatively low concentrations, yet provide a clear, strong signal. The present invention also provides novel MRI agents which include paramagnetic metal species that enhance magnetic resonance results.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for obtaining magnetic resonance images of body organs and tissues which comprises:
   (a) administering to a mammal having organs and tissues, a diagnostically effective amount of a carbon cluster in a pharmaceutically acceptable carrier, said carbon cluster having a formula $C_n$, wherein n is in the range from about 320 to about 100, said carbon cluster incorporating therein a paramagnetic metal species and said carbon cluster being at least partially hydrogenated; and
   (b) imaging the organs and tissues.

2. A method for obtaining magnetic resonance images as defined in claim 1, wherein the paramagnetic metal species is selected from a group of elements having atomic numbers of 21–25, 27–29, 42–44, and 58–70 and a valence, z, in the range from $1+$ to $3+$.

3. A method for obtaining magnetic resonance images a defined in claim 1, wherein the paramagnetic metal species is chromium (III), manganese (II), manganese (III), iron (III), praseodymium (III), neodymium (III), samarium (III), ytterbium (III), gadolinium (III), terbium (III), dysprosium (III), holmium (III), or erbium (III).

4. A method for obtaining fluorine-19 magnetic resonance images of body organs and tissues which comprises:
   (a) administering to a mammal having organs and tissues, a diagnostically effective amount of a carbon cluster in a pharmaceutically acceptable carrier, said carbon cluster having a formula $C_nF_m$, wherein n is in the range from about 30 to about 100 and $m \leq n$, said carbon cluster incorporating therein a paramagnetic metal species; and
   (b) imaging the organs and tissues.

5. A method for obtaining fluorine-19 magnetic resonance images as defined in claim 4, wherein n is in the range from about 50 to 70.

6. A method for obtaining fluorine-19 magnetic resonance images as defined in claim 4, wherein the perfluorinated carbon cluster has the formula $C_{60}F_{60}$.

7. A method for obtaining fluorine-19 magnetic resonance images as defined in claim 4, wherein the paramagnetic metal species is selected from a group of elements having atomic numbers of 21–25, 27–29, 42–44, and 58–70 and a valence, z, in the range from $1+$ to $3+$.

8. A method for obtaining fluorine-19 magnetic resonance images as defined in claim 4, wherein the paramagnetic metal species is chromium (III), manganese (II), manganese (III), iron (III), praseodymium (III), neodymium (III), samarium (III), ytterbium (III), gadolinium (III), terbium (III), dysprosium (III), holmium (III), or erbium (III).

9. A diagnostic composition suitable for enteral or parenteral administration to a warm-blooded animal, which comprises:
   a diagnostically effective amount of a carbon cluster of the formula $C_n$, wherein n is in the range from about 30 to about 100, said carbon cluster incorporating therein a paramagnetic metal species and said carbon cluster being at least partially hydrogenated; and
   a pharmaceutically acceptable carrier.

10. A diagnostic composition as defined in claim 9, wherein n is in the range from about 50 to 70.

11. A diagnostic composition as defined in claim 9, wherein the paramagnetic metal species is selected from a group of elements having atomic numbers of 21–25, 27–29, 42–44, and 58–70 and a valence,, z, in the range from $1+$ to $3+$.

12. A diagnostic composition as defined in claim 9, wherein the paramagnetic metal species is chromium (III), manganese (II), manganese (III), iron (III), praseodymium (III), neodymium (III), samarium (III), ytterbium (III), gadolinium (III), terbium (III), dysprosium (III), holmium (III), or erbium (III).

13. A diagnostic composition suitable for enteral or parenteral administration to a warm-blooded animal, which comprises:
   a diagnostically effective amount of a carbon cluster of the formula $C_nF_m$, wherein n is in the range from about 30 to about 100 and $m \leq n$, said carbon cluster incorporating therein a paramagnetic metal species; and
   a pharmaceutically acceptable carrier.

14. A diagnostic composition as defined in claim 13, wherein n is in the range from about 50 to 70.

15. A diagnostic composition as defined in claim 13, wherein the perfluorinated carbon cluster has the formula $C_{60}F_{60}$.

16. A diagnostic composition as defined in claim 13, wherein the paramagnetic metal species is selected from a group of elements having atomic numbers of 21–25, 27–29, 42–44, and 58–70 and a valence, z, in the range from $1+$ to $3+$.

17. A diagnostic composition as defined in claim 13, wherein the paramagnetic metal species is chromium (III), manganese (II), manganese (III), iron (III), praseodymium (III), neodymium (III), samarium (III), ytterbium (III), gadolinium (III), terbium (III), dysprosium (III), holmium (III), or erbium (III).

* * * * *